(12) United States Patent
Atchison (10) Patent No.: US 9,851,284 B2
(45) Date of Patent: Dec. 26, 2017

(54) TANDEM SCOOP AND METHOD FOR PIPELINE SAMPLING

(71) Applicant: Martin Atchison, Manvel, TX (US)

(72) Inventor: Martin Atchison, Manvel, TX (US)

( * ) Notice: Subject to any disclaimer, the term of this patent is extended or adjusted under 35 U.S.C. 154(b) by 584 days.

(21) Appl. No.: 14/282,433

(22) Filed: May 20, 2014

(65) Prior Publication Data

US 2014/0251007 A1    Sep. 11, 2014

Related U.S. Application Data

(63) Continuation of application No. 14/187,901, filed on Feb. 24, 2014, now Pat. No. 9,562,839.

(60) Provisional application No. 61/769,896, filed on Feb. 27, 2013.

(51) Int. Cl.
*G01N 1/20* (2006.01)
*G01N 9/36* (2006.01)
*F16L 9/00* (2006.01)
*F16L 41/08* (2006.01)
(Continued)

(52) U.S. Cl.
CPC ............... *G01N 9/36* (2013.01); *F16L 9/00* (2013.01); *F16L 27/00* (2013.01); *F16L 41/08* (2013.01); *F16L 41/084* (2013.01); *F16L 41/10* (2013.01); *G01N 1/20* (2013.01); *G01N 1/2035* (2013.01);
(Continued)

(58) Field of Classification Search
CPC ......... F16L 41/08; F16L 41/084; F16L 41/10; F16L 27/00; G01N 1/20; G01N 1/2035; G01N 9/36

USPC .... 73/32 R, 863.85, 864.63, 864.51, 863.64, 73/863.41, 863.43, 863.61, 863.71, 73/863.73, 863.81, 863.86, 73/863.51–863.52, 864, 864.02, 864.64, 73/864.81, 864.83, 864.91; 29/256, 263; 285/93, 192, 144.1; 141/324; 137/205.5; 366/140
See application file for complete search history.

(56) References Cited

U.S. PATENT DOCUMENTS

| 15,560 | A | | 5/1856 | Fetter |
|---|---|---|---|---|
| 1,101,574 | A | * | 6/1914 | Shephard ............. A01C 23/024 137/205.5 |
| 1,334,130 | A | | 3/1920 | Blanchard |

(Continued)

OTHER PUBLICATIONS

Code of Federal Regulations: Protection of Environment, Jul. 1, 1992, 40 Parts 61 to 80.*

(Continued)

*Primary Examiner* — Peter Macchiarolo
*Assistant Examiner* — David L Singer
(74) *Attorney, Agent, or Firm* — Kenneth L. Nash; Thomas D. Nash (57) ABSTRACT

A bi-directional flow scoop system and/or tandem system is mountable to a pipeline operable for receiving and returning a fluid flow from the pipeline. A first tubular is mounted so that the first tubular extends into the pipeline. The scoop end comprises a bend leading to a first face with a first opening for communication with the fluid flow. A second tubular is mounted with a second opening for communication with the fluid flow. The bi-directional scoop is configurable to provide fluid flow in two directions when mounted to the pipeline. In one embodiment, the bi-directional flow scoop system and/or tandem system a flange is provided for (Continued)

separately mounting the first and second tubulars and in another embodiment the second tubular is mounted within the first tubular.

10 Claims, 9 Drawing Sheets

(51) Int. Cl.
*F16L 27/00* (2006.01)
*F16L 41/10* (2006.01)

(52) U.S. Cl.
CPC ...... *Y10T 137/0402* (2015.04); *Y10T 137/598* (2015.04)

(56) References Cited

U.S. PATENT DOCUMENTS

| | | | |
|---|---|---|---|
| 2,240,648 A * | 5/1941 | Hartman | A61L 2/00 137/592 |
| 2,301,280 A * | 11/1942 | Howe | F16L 19/06 277/622 |
| 2,463,707 A | 3/1949 | Matousek | |
| 2,503,826 A | 4/1950 | Robert | |
| 2,508,763 A | 5/1950 | Mercier | |
| 2,922,441 A | 1/1960 | Ferdinand | |
| 2,926,527 A | 3/1960 | Crandall | |
| 3,101,619 A | 8/1963 | Hunter | |
| 3,765,226 A * | 10/1973 | Strickland | G01N 1/2035 73/53.01 |
| 3,776,274 A * | 12/1973 | Riley | A01C 23/042 137/205.5 |
| 4,018,089 A * | 4/1977 | Dzula | G01N 1/2035 73/863.58 |
| 4,152,936 A | 5/1979 | Boykin | |
| 4,391,152 A | 7/1983 | Ellett | |
| 4,606,218 A * | 8/1986 | Chisman, III | G01F 25/0015 73/1.17 |
| 4,631,967 A | 12/1986 | Welker | |
| 4,633,713 A | 1/1987 | Mesnard | |
| 4,717,159 A * | 1/1988 | Alston | G01F 15/185 277/314 |
| 4,776,618 A | 10/1988 | Barree | |
| 4,928,536 A | 5/1990 | Welker | |
| 5,009,113 A | 4/1991 | Kamrat | |
| 5,138,755 A | 8/1992 | Evans | |
| 5,161,417 A * | 11/1992 | Strong | G01N 1/2035 73/863.31 |
| 5,410,920 A | 5/1995 | Westwick | |
| 5,922,972 A | 7/1999 | Maurin | |
| 5,974,858 A * | 11/1999 | Francisco, Jr. | G01N 9/002 73/32 A |
| 6,357,470 B1 | 3/2002 | Evans | |
| 6,390,670 B1 | 5/2002 | Nimberger | |
| 7,066,496 B2 | 6/2006 | Williams | |
| 8,647,483 B2 * | 2/2014 | Andrews | C02F 1/4674 137/599.15 |
| 2003/0070718 A1* | 4/2003 | Benham | F15D 1/14 137/861 |
| 2004/0161804 A1 | 8/2004 | McCash | |
| 2006/0141637 A1* | 6/2006 | Hassell, Jr. | G01N 1/2035 436/180 |
| 2008/0098829 A1 | 5/2008 | Nathan | |
| 2009/0145488 A1 | 6/2009 | Hoskisson | |
| 2012/0011923 A1 | 1/2012 | Evans | |
| 2014/0252759 A1 | 9/2014 | Atchison | |

OTHER PUBLICATIONS

ASME B31.8: Gas Transmission and Distribution Piping Systems, 2004, American Society of Mechanical Engineers.*
Brad Frank, Sav Money When Ordering Tools, TheFabricator.com/ The Tibe and Pipe Journal, Nov. 21, 2002, Issue 431, USA.
Compression Fitting, Wikipedia, Feb. 5, 2016, Information last updated Nov. 2, 2015, USA.
Don Sextro, Installation and Operation of Densitometers, Class No. 2205, Targa Resources, Houston, Texas, USA.
Oil and Gas Pipelines, Tenaris Technical Information Page (www.tenaris.com/en/Products/OnShoreLinePipe/OilAndGasPipeline.aspx), Feb. 5, 2016.
Why Steel: Strength, Toughness, Ductility, and Weldability, Why Steel, Feb. 5, 2016.
Pipelines, OnePetro.org, Feb. 5, 2016.
Seamless Pipe, Drilling Lexicon, iadlexicon.org, Feb. 5, 2016.
Saf T Flo, Instruction manual: Retractable Sampling Probe, Apr. 4, 2012.
Saf T Flow, Sampling Probes, Oct. 16, 2008, Archived Version.
Swagelok, An Installer's Pocket Guide for Swagelok Tube Fittings, Mar. 2004.
Swagelok, Sample Probe Module Application Guide, Sep. 2011, pp. 12-14.

* cited by examiner

TANDEM SCOOP AND METHOD FOR PIPELINE SAMPLING

This application is a continuation of US application Ser. No. 14/187,901 filed Feb. 24, 2014 and claims benefit of US Provisional Patent Application No. 61/769,896 filed Feb. 27, 2013.

CROSS REFERENCE TO OTHER PATENT APPLICATIONS

None.

BACKGROUND OF THE INVENTION (1) Field of the Invention

The present invention relates generally to scoops for measuring the density of fluid in pipelines and, more specifically, in one or more embodiments to novel scoop configurations that provide improved flow and more accurate density readings of the fluid.

(2) Background of the Invention

Scoops have been utilized for decades to monitor the density of the fluids in pipelines. The density of the fluids relates to how much product is transported. Accuracy of the density readings is important because the result can affect the prices paid for shipping product through the pipeline, which prices can be significant. Therefore both the pipeline companies and the users of the pipelines desire to obtain the most accurate readings as possible.

Despite the long felt need for accurate readings, prior art scoops have long had many problems that have not been resolved. Prior art scoops may not produce enough fluid flow to obtain a good sample. In some cases, differential pressure devices such as pumps are required when using prior art scoops. Differential pressure devices can introduce fluid contamination as well as increase the size and complexity of the density measurement systems.

Scoops used to take samples can be inaccurate because fluid beneath the valve is static. Therefore the sample taken may not be representative of fluid in the pipeline at the moment the sample is taken and/or can be contaminated with fluid that has accumulated beneath the valve.

In some cases, scoops are mounted utilizing a threaded receptacle that may be secured and sealed to the pipeline utilizing one of three sanctioned connections 1) pipe threads & sealant; 2) socket weld or 3) butt-weld. The threads in the threaded receptacle provide a seal with the threaded receptacle. However, mounting the scoop to the threaded receptacle can provide difficulties in orienting in the pipe in a manner that maximizes flow through the scoops.

Another problem is that scoops must on occasion be removed from the pipeline to allow pigs to pass through the pipeline. Removing and reintroducing the scoops can be time consuming with corresponding lost use of the pipeline.

Those of skill in the art have long sought a better scoop design and better scoop systems to provide more accurate readings. Consequently, those of skill in the art will appreciate the present invention, which addresses the above and/or other problems.

SUMMARY OF THE INVENTION

Accordingly, it is an object of the present invention to provide improved scoop designs.

Another possible object of the invention is to provide a scoop design that is compact and improves flow of product through the scoop.

Yet another object of the invention is to provide a scoop design that bends a pipe so the pipe remains straight but the face of the scoop is directed laterally into the flow.

Yet another object of the invention is to provide a scoop design utilizing a tubular to pipe connector wherein the pipe connector threads onto a mating threaded connector on the pie but provides a compressible connection that allows rotation of the scoop for orientation of the scoop prior to tightening of the connector.

Yet another object is providing a retractable pipe scoop design.

Yet another object is to provide a compact bi-directional tandem scoop design.

Yet another object is to provide an even more compact single scoop pipe bi-directional scoop design.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE INVENTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1A:
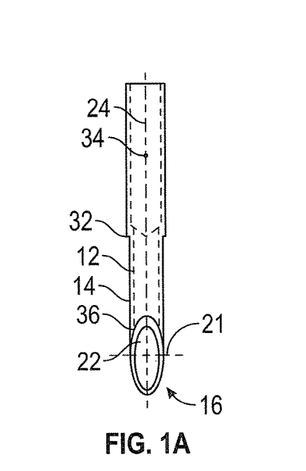
FIG. 1A is a front elevational view, partially in hidden lines, of a scoop to obtain a product sample in accord with one possible embodiment of the present invention.
Figure 1B:
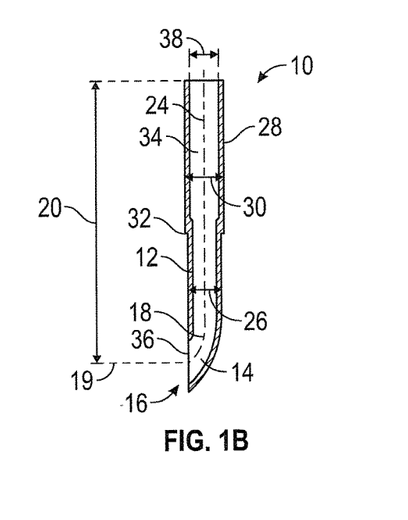
FIG. 1B is a side elevational view, in cross-section, of the scoop of FIG. 1A in accord with one possible embodiment of the present invention.

FIG. 1A and FIG. 1B show a bended scoop design 10 that comprises a single seamless pipe or tubular with first tubular portion 12 adjacent scoop end 14. Second tubular portion 28 has a larger outer diameter 30 than outer diameter 26 of first tubular portion 12.

One possible method of the present invention involves machining the single tubular pipe to reduce the original pipe stock diameter to outer diameter 30 of second tubular portion 28. Then further machining reduces the outer diameter of first tubular portion 12 to outer diameter 26. Shoulder 32 is formed between first tubular portion 12 and second tubular portion 28. The scoop end is then bent as shown to provide scope face 16 that is oriented laterally and preferably perpendicular with respect to centerline 24 as indicated by line scoop face centerline 19.

Accordingly, the bending of first tubular portion 12 of scoop design 10 results in forming scoop face 16. In one embodiment, scoop face 16 provides opening 22 (See FIG. 1A) that is preferably perpendicular and at least angled with respect to tubular centerline 24 as indicated by the perpendicular scoop face centerline 20. At least a portion and preferably the centerline of scoop face 16 is coaxial with a surface of the straight portion of first tubular portion 12. Scoop face 16 comprises outline 36 that preferably defines a plane that is parallel to axis 24. Outline 36 can be elliptical or substantially elliptical in shape. A smaller axis 21 of the ellipse of outline 36 is substantially equal to an internal diameter 38 of scoop design 10. The larger axis of the ellipse varies with respect to the bend radius.

First tubular portion 12 is bent to provide bend radius 18 as shown in FIG. 1B. Bend radius 18 is between two times and four times of scoop 10 and preferably two and four times that of outer diameter 30 of second tubular portion 28 although conceivably between two and four times outer diameter 26 of first tubular portion 12. In another embodiment, bend radius 18 may be between two and three times outer diameter 28. In another embodiment, bend radius 18 may be between 2.3 and 2.7 times outer diameter 28 and/or may be within a smaller range or larger range or outside these ranges. The bend radius may vary depending on the outer diameter of first tubular portion 12. The bend radius affects the fluid flow characteristics and these ranges have been found to provide the best fluid flow through bended sample scoop design 10.

While the features of the scoop face 16 are defined herein in terms of geometrical features such as planes, ellipses, perpendicular, and so forth, it is understood that the features are not geometrically perfect and could have variations, e.g., with 2 and/or to 5 and/or to 10 and/or to 20 range degree variations and any range there between. However, the design may fall outside these ranges and may include corresponding non-linearities.

Figure 2A:
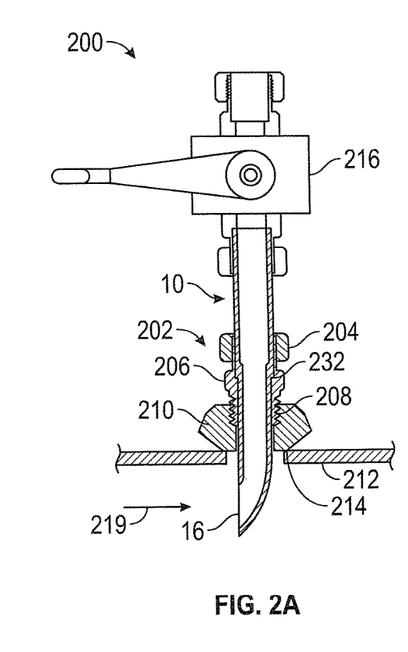
FIG. 2A is a side elevational view, partially in cross-section, showing the scoop of FIG. 1A and 1B mounted to a pipe utilizing a tubular to pipe connection in accord with one possible embodiment of the invention.

Scoop 10 provides mark 34 shown in FIG. 1A that is aligned with the center of scoop face 16. This allows alignment of scoop face 16 with respect to the center line of the pipeline as discussed with respect to FIG. 2. In other words, scoop 10 can be rotated to provide that mark 34 is in-line with the axis of the pipeline, whereupon the scoop is fixed in that orientation as discussed hereinbefore.

Scoop design 10 is preferably provided in three different sizes with outer diameter 30 ranging from one inch to one and one-half inches.

FIG. 2A shows the scoop design 10 mounted in an orientable or alignable sampling assembly 200 that permits alignment of scoop face 16 with respect to the pipeline axis and flow arrow 219. In this way, flow or fluid pressure into scoop face 16 can be maximized. Orientable sampling assembly 200 is believed to be yet another significant improvement over the prior art.

Alignable or orientable sampling assembly 200 preferably utilizes tubular to pipe connector 202, which is commercially available off the shelf, in a highly unique manner. Pipe connectors require threads. Tubular to pipe connector 202 comprises a tubular pipe connection with ferrule seals 218, 220 and threaded pipe connection with threads 208. Accordingly a tubular to threaded connection comprises a connection from a non-threaded cylinder to a threaded connection. Tubular to pipe connector 202 comprises compression nut 204, which is threadably securable to pipe connector 206 utilizing threads 222. Pipe connector 206 provides pipe connection with threads 208 to receptacle 210, which is provided on pipe 212. Receptacle 210 utilizes seal 214 with pipe 212, which can be one of three sanctioned connections 1) pipe threads & sealant; 2) socket weld or 3) butt-weld. Valve 216 may be secured to an upper end of scoop design 10 and may be utilized to provide samples of the pipe fluid as desired.

Figure 2B:
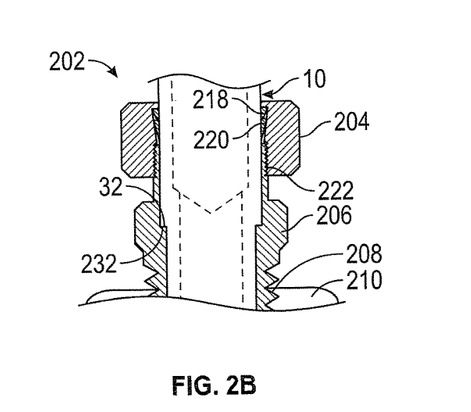
FIG. 2B is an enlarged elevational view, in cross-section, showing a tubular to pipe in accord with one possible embodiment of the invention.

FIG. 2B shows an enlarged view of tubular to pipe connector 202. It will be seen that compression nut 204 can be utilized to compress ferrules 218 and 220 for sealing around the tubular body of scoop design 10. As compression nut 204 is tightened by rotation on threads 222, a seal is formed, which may be referred to as a first seal in the claims, around the tubular body of scoop design 10. Further, threads 208, which may be referred to as a second seal in the claims, are tightened to provide a seal between receptacle 210 and pipe connector 206. Shoulder 32, shown in FIG. 1A and 1B, seats onto seat 232 formed within tubular to pipe connector 202.

In operation of one embodiment of alignment or orientation, scoop 10 is placed in tubular to pipe connector 202 until shoulder 32 of scoop 10 engages seat 232 in tubular to pipe connector 202. Scoop 10 can then be rotated to orient scoop face 16 within pipe 212 for receiving flow in pipe 212 as indicated by arrow 219. This is accomplished utilizing mark 34 shown in FIG. 1A that is aligned with the center of scoop face 16. Once scoop face 16 is aligned with respect to pipe 212, then compression nut 204 can be tightened to seal around the tubular body of scoop 10. Two scoops like that of FIG. 2A may be used to provide a measurement loop for bi-directional flow out of pipe 212 and then return the flow to the pipe after measurements are made as discussed hereinafter.

FIG. 3A, FIG. 3B, FIG. 3C and FIG. 3D show aspects of retractable scoop and yoke design pipeline scoop 300 in accord with one embodiment of the present invention. Retractable pipeline scoop 300 preferably utilizes scoop design 10, which allows easy movement into and out of pipeline 303 because scoop design 10 has the same OD as a single tubular. While other types of scoops could possibly be utilized, scoop design 10 is probably the best type of scoop for use in retractable pipeline scoop 300.

As discussed herein with other embodiments of the invention, two retractable pipeline scoops could be connected together to form a flow loop to measure pipeline fluid with a densitometer, flow meter, prover, and/or takes samples as desired.

Unlike prior art scoops which may be time consuming to remove when a pig is sent down the pipeline, retractable pipeline scoop 300 can be easily retracted from the pipeline and inserted into the pipeline without requiring loss of the seal. Pipeline downtime is therefore greatly reduced.

In this embodiment, upper yoke 305 and lower yoke 304 are mounted on yoke screws 306 and 308. Yoke screws 306 and 308 extend through openings 310 and 312 in overall yoke design 302 shown in FIG. 3D. Scoop 10 extends through but is fixed to opening 314 in upper yoke 305. Openings 311 and 313 in upper yoke 305 are threaded. The corresponding openings 316, 318 are not threaded. Opening 320 in lower yoke 304 allows scoop 10 to slidably move therethrough as seen in FIG. 3A, FIG. 3B, and FIG. 3C.

Accordingly, one main difference be&een upper yoke 305 and lower yoke 304 is that openings 311 and 313 are threaded whereas openings 316 and 318 are not. As well, upper yoke 305 is secured to scoop 10 whereas lower yoke 304 allows scoop 10 to move therethrough and includes an O-ring seal when the tubular to pipe connector sealing is not yet connected (See FIG. 3C) prior to operation as shown in FIG. 3A (scoop removed from pipeline) and FIG. 3B (scoop extended into pipeline).

As yoke screws 306 and 308 are rotated, yoke 305 is urged to move. For manual operation, a few turns can be applied to one yoke screw and then applied to the other yoke screw. The operation could be automated.

Figure 3A:
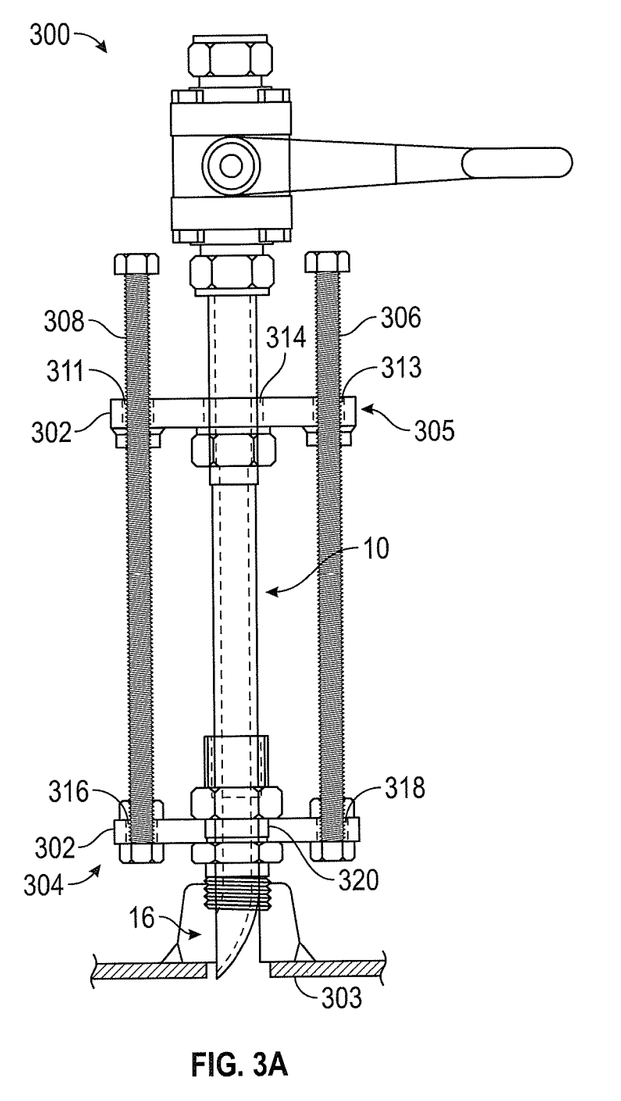
FIG. 3A is a side elevational view, partially in cross-section, showing a retractable scope and yoke design that in a retracted position with respect to a pipeline in accord with one possible embodiment of the present invention.
Figure 3B:
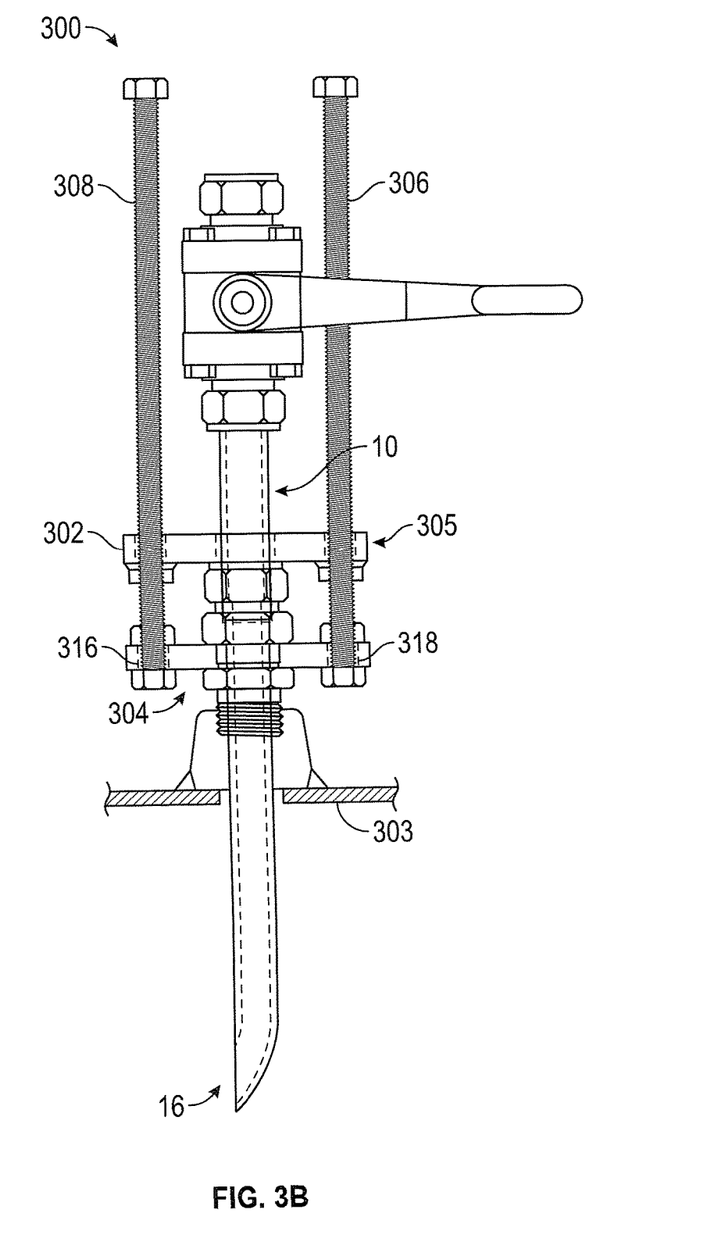
FIG. 3B is a side elevational view, partially in cross-section, showing the retractable scope and yoke design of FIG. 3A in an extended position with respect to a pipeline in accord with one possible embodiment of the present invention.
Figure 3C:
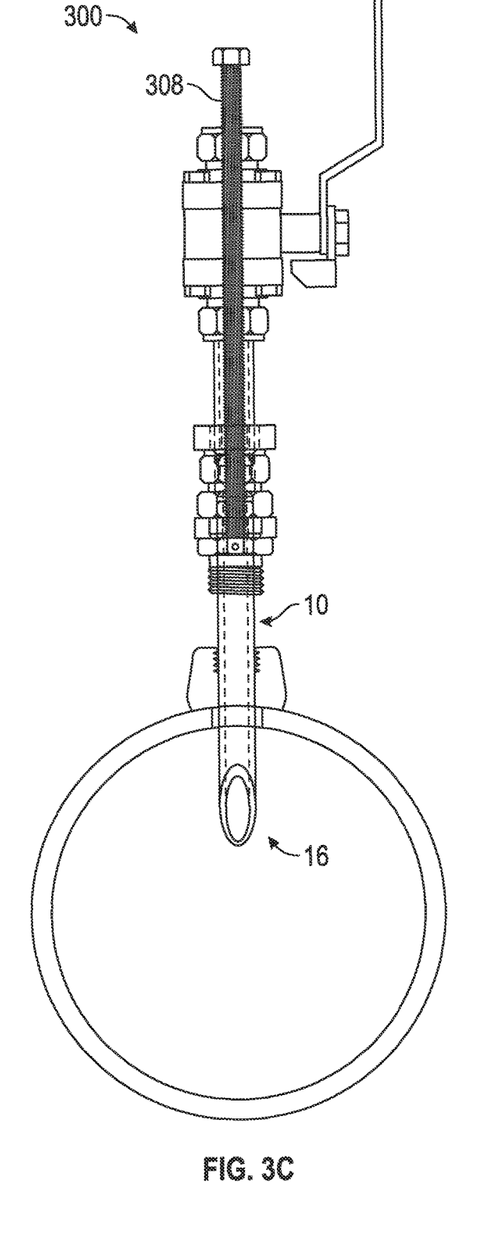
FIG. 3C is a front elevational view, partially in hidden lines, showing the retractable scoop and yoke design of FIG. 3A and 3B prior to mounting a threaded connector to the pipe connector in accord with one possible embodiment of the invention.

The sealing of FIG. 2 is utilized during operation as shown in FIG. 3A and FIG. 3B but utilizes O-rings at 320 prior to connection of the tubular to pipe seals as indicated in FIG. 3C. O-rings may comprise suitable resilient O-ring seal material. The O-ring seal preferably utilizes a smoother finish on the scoop pipe surface.

Figure 3D:
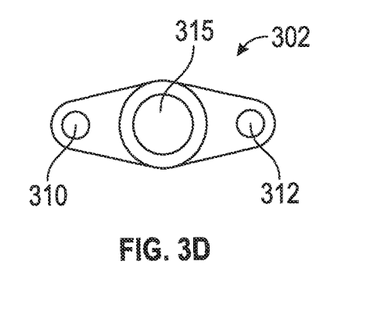
FIG. 3D is a top view of a yoke component for a retractable scoop in accord with one possible embodiment of the present invention.

FIG. 3D shows the general plan layout of upper yoke 305 and lower yoke 304 with the differences discussed hereinbefore for openings 310, 312, and 315.

FIG. 4, FIG. 5, FIG. 6, FIG. 9A, and FIG. 9B show various compact tandem scoop configurations that utilize two scoops oriented in opposite directions on a single flange in the pipeline for sampling and/or densitometer and/or flow meter fluid flow loops. The measurement flow loops discussed hereinafter provide sufficient flow of fluid from the pipeline without the need for differential pressure devices (such as pumps or the like), thereby significantly reducing the size, complexity, and fluid contamination. In a preferred embodiment, the compact sampling loops utilize scoop 10 discussed hereinbefore but the present invention is not limited to those scoop designs.

Figure 4:
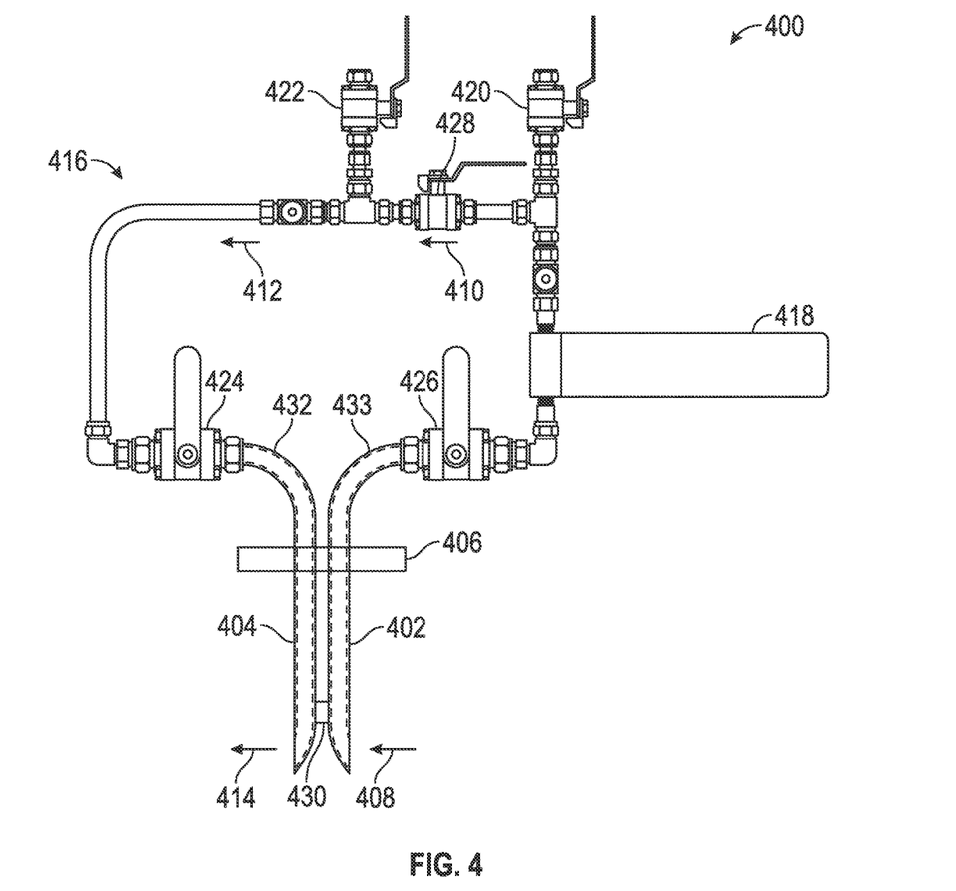
FIG. 4 is a side elevational view, partially in hidden lines, showing one type of compact sampling and/or densitometer loop with tandem scoops in accord with one possible embodiment of the present invention.

In FIG. 4 there is shown flow axis aligned tandem scoop system 400 mounted to a single flange 406. Scoops 402 and 404 extend through top flange 406, which may be a typical 3"-600# mounting flange. Scoops 402 and 404 are sealed by top flange 406, which itself is sealingly mounted to the pipeline. Flow proceeds through flow loop 416 as indicated by arrows 408, 410, 412, and 414 whereby flow is taken out of the pipeline and then returned to the pipeline. Well known configurations of the flow loop may comprise densitometer 418, sampling valves 420, 422, and flow control valves 424, 426, and 428.

As per standard API requirements, scoops 402 and 404 are designed to have a length that access the middle $\frac{1}{3}^{rd}$ of flow.

In tandem scoop system 400, scoops 402 and 404 are positioned upstream and downstream of each other in line with the axis of the pipe and oriented in opposite directions. Scoops 402 and 404 are mounted into a single flange 405 and secured together at a lower end by mounting member 430. Bends 432 and 433 are provided to allow the various connections to be made to valves 426 and 424. Accordingly, an entire sampling system can extend through a single flange mounting.

Figure 6:
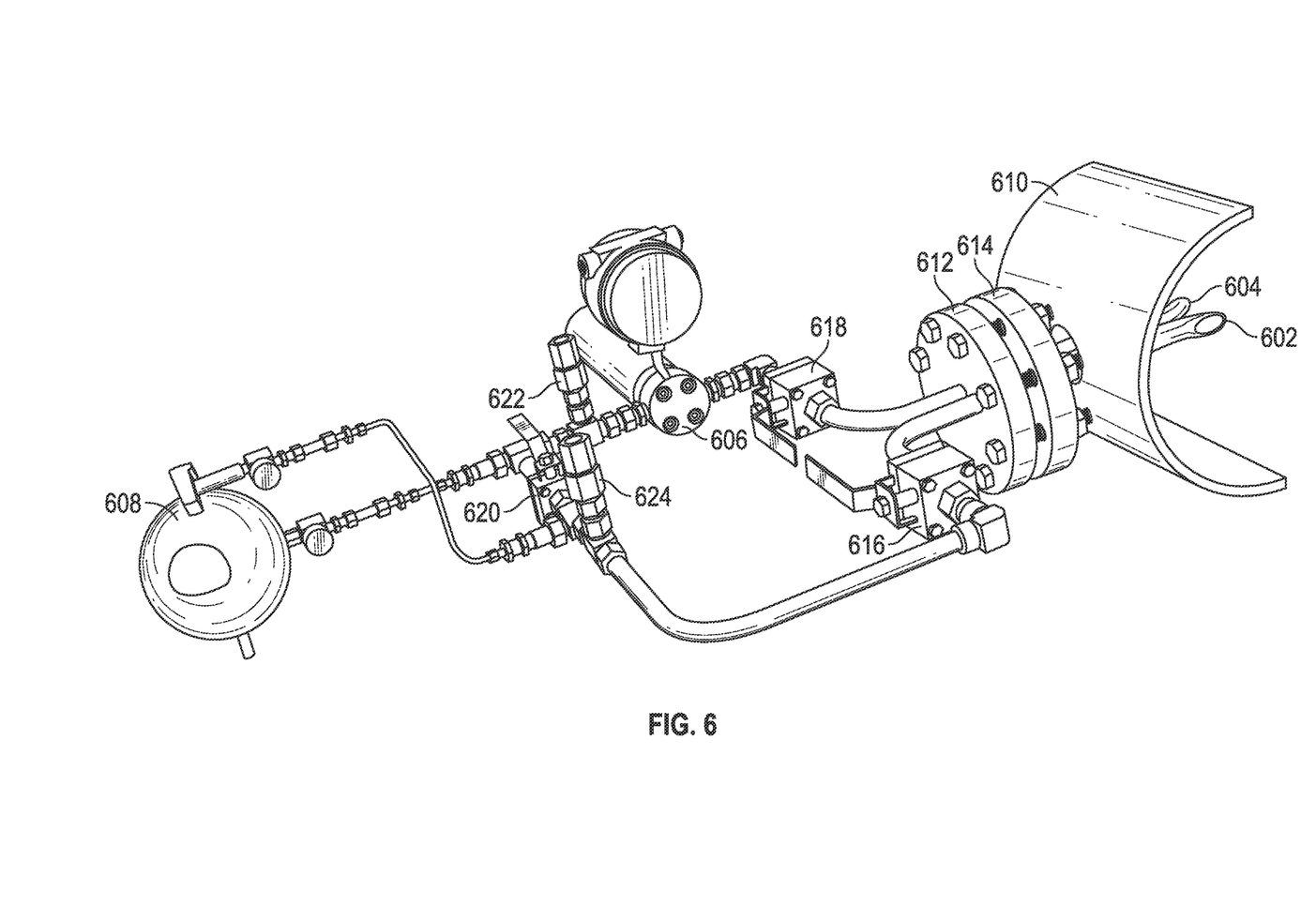
FIG. 6 is a perspective view showing a prover, sampling and/or densitometer loop with tandem scoops in accord with one possible embodiment of the present invention.

FIG. 6 shows a perspective view of flow axis aligned scoops 602 and 604 with connections to densitometer 606 and prover 608. A half portion of pipeline 610 is provided with flange 612 secured to flange mounting 614 provided on pipeline 610. Valves 616, 618, 620, and/or other valves can be used to control fluid flow through the measurement flow loop. Fluid samples can be taken at 622 and 624.

Figure 5:
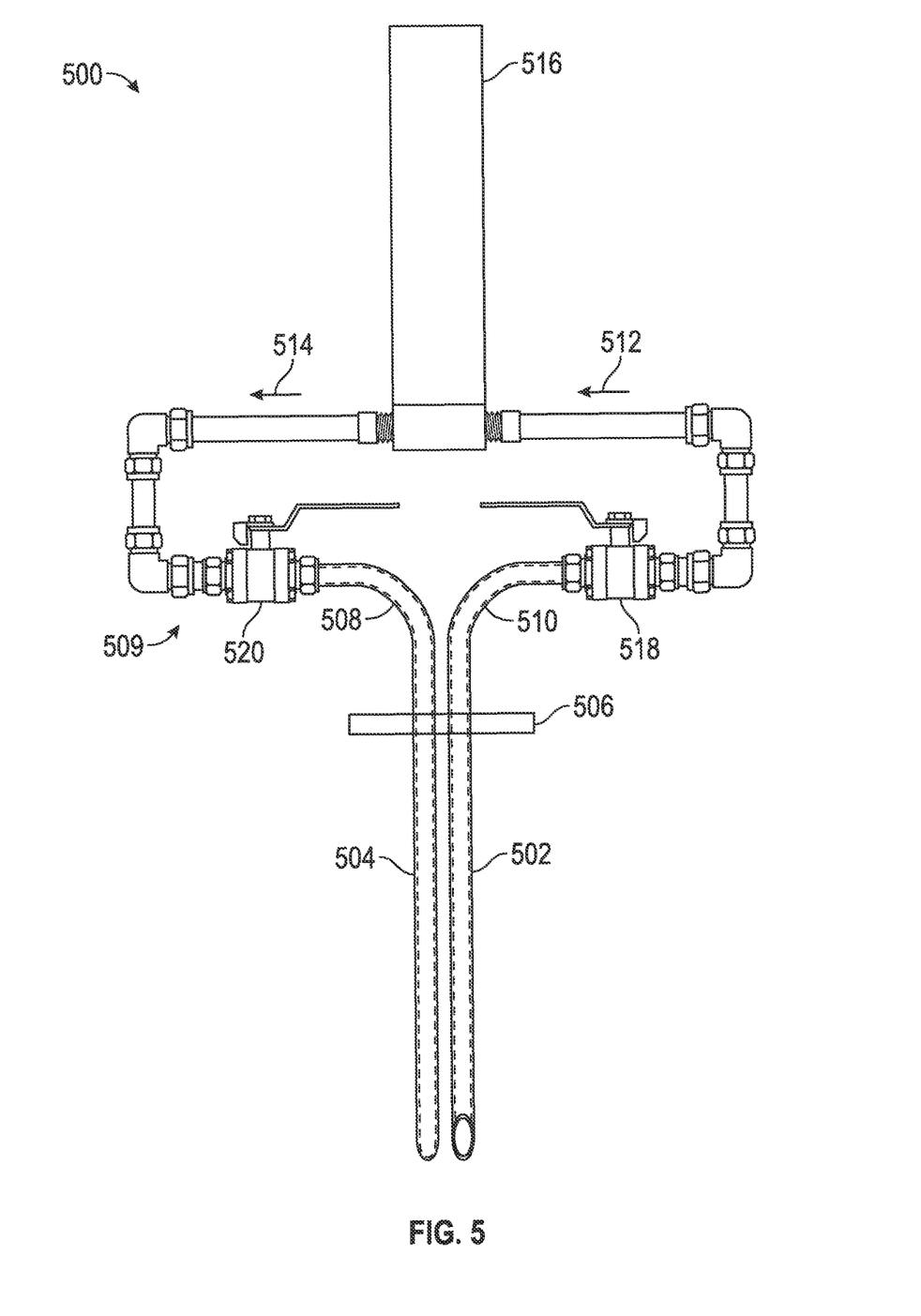
FIG. 5 is a front elevational view, partially in hidden lines, showing another type of compact sampling and/or densitometer loop with tandem scoops in accord with one possible embodiment of the present invention.

Referring now to FIG. 5, perpendicular mount tandem scoop system 500 provides scoops 502 and 504 positioned side by side or perpendicular with respect to the axis of the pipeline. In this embodiment flange 506 may comprise a 2"-150# mounting flange. Bends 508 and 510 permit connection to flow loop 506, which in this embodiment comprises densitometer 516 and valves 518, 520. Flow may proceed into and out of the pipeline in a direction through flow loop 509 with flow direction indicated by arrows 512 and 514.

Figure 9A:
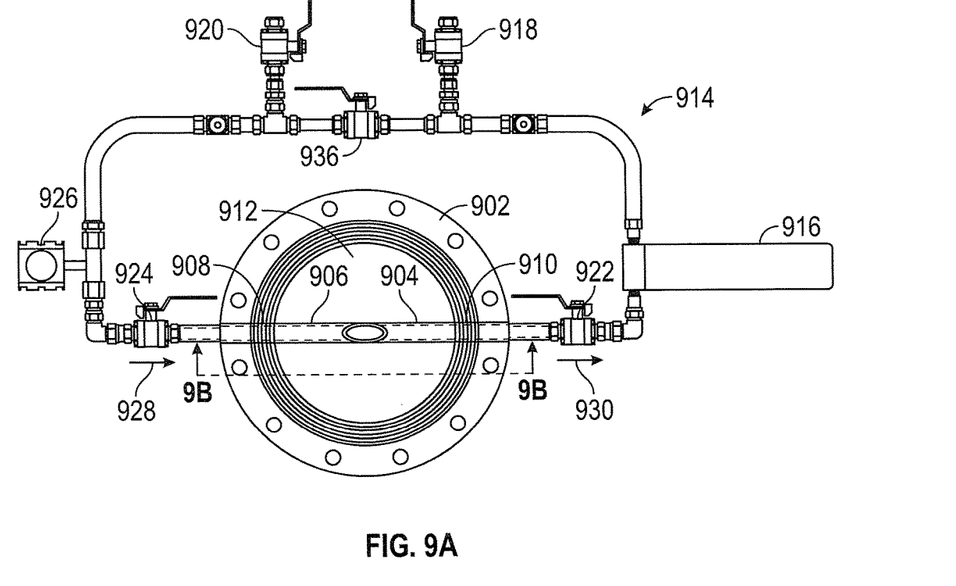
FIG. 9A is a side elevational view of wafer mounted tandem scoops that provides a sampling and/or densitometer and/or flow meter loop in accord with one possible embodiment of the present invention.
Figure 9B:
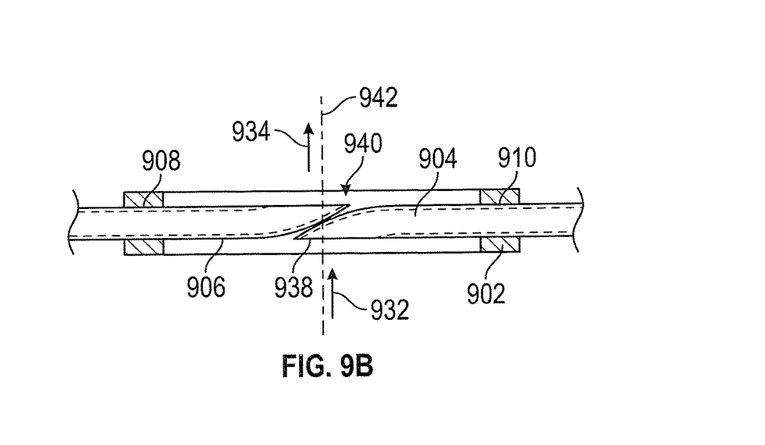
FIG. 9B is a cross-sectional view of FIG. 9A along lines A-A in accord with one possible embodiment of the present invention.

FIG. 9A and FIG. 9B show wafer mount tandem scoop system 900. In two possible examples, wafer flange 902 may comprise a 12" 150# or 10" 900# wafer flange. The wafer flange can be mounted between flanges in the pipeline so that wafer flange 902 surrounds the flow area going through the pipeline. In this example, scoops 904 and 906 are axially aligned with respect to the pipeline axis and extend from opposite directions and from opposite sides of wafer flange 902. Scoops 904 and 906 are sealed and mounted within wafer flange 902 as indicated at 908 and 910 and are essentially in-line with plane 912 defined by wafer flange 902.

In wafer mount system 200, it is not necessary to provide a bend in scoops 904 and 906. Flow loop 914 can comprise densitometer 916, sampling valves 918, 920, flow meter 926, and control valves 922, 936, 924. Fluid flows through loop 914 in the direction indicated by arrows 928 and 930. As indicated in FIG. 9B, flow proceeds out of the pipeline in the direction shown by arrow 934 and into the pipeline in the direction indicated by arrow 932. Scoop faces 938 and 940 are axially aligned with pipeline centerline 942.

Accordingly, the present invention provides three compact tandem scoop system 400, 500, and 900 that mount two scoops to a single flange.

Figure 7:
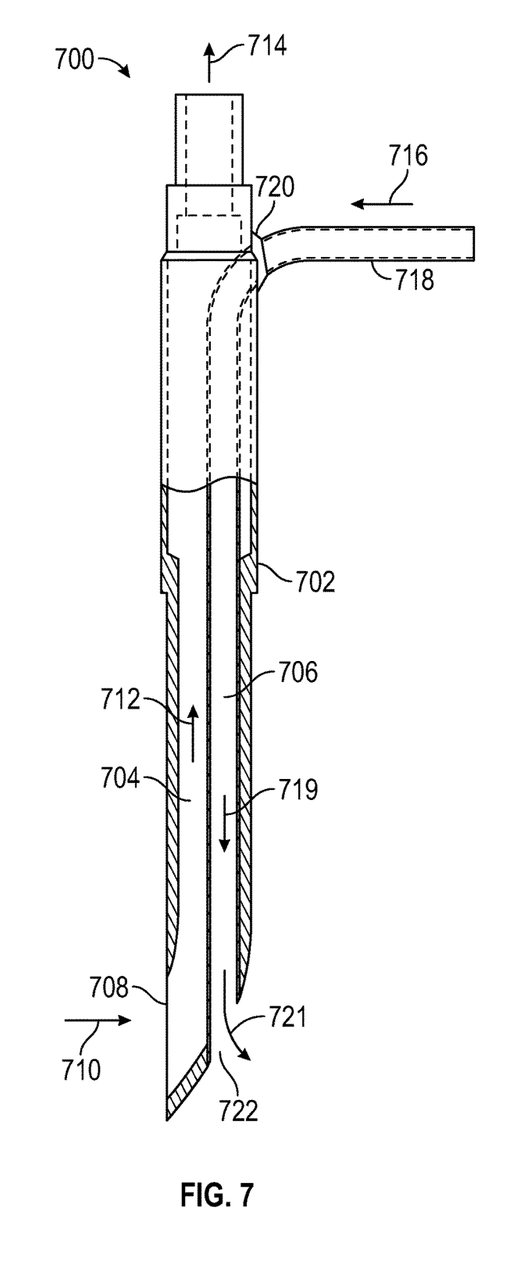
FIG. 7 is side view, partially in hidden lines of a first type of bidirectional flow single tubular flow scoop that provides a sampling and/or densitometer and/or prover loop in accord with one possible embodiment of the present invention.
Figure 8:
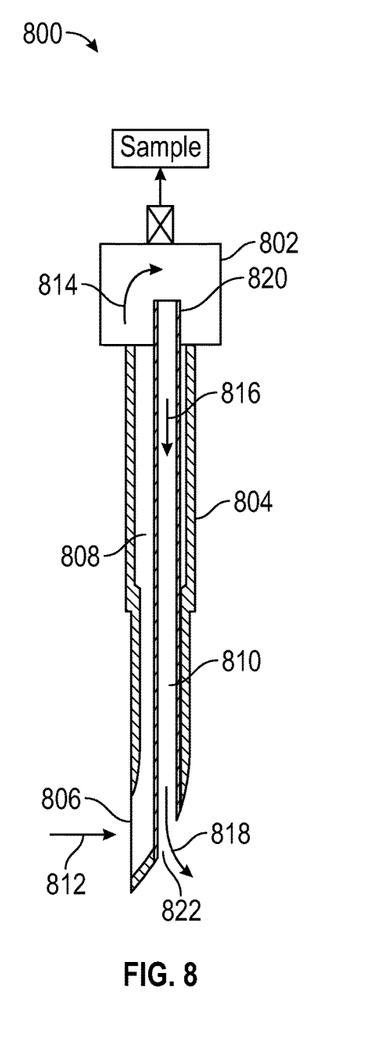
FIG. 8 is a side view, partially in cross-section, showing a second type of bidirectional flow single tubular flow scoop with a mixing chamber in accord with one possible embodiment of the present invention.

FIG. 7 and FIG. 8 show bi-directional flow scoops formed within a single pipe. Bi-directional flow loop scoop 700 provides a single tubular scoop that can be utilized to provide a flow loop for density, proving, sampling, and the like as discussed hereinbefore.

Bi-directional mixing scoop 800 provides a single tubular scoop that can be utilized to provide a mixing chamber with continually refreshed fluid so that the sample is representative of fluid in the pipeline at the time the sample is taken avoiding the problems of trapped sample at the sampling valve as discussed hereinbefore.

Bi-directional flow loop scoop 700 utilizes single pipe 702 with two separate internal flow paths 704 and 706. The external shape of single pipe 702 is similar or the same as described by scoop 10 discussed hereinbefore so tubular to pipe connector can be utilized for sealing and orientation. Flow proceeds from the pipeline into scoop face 708 as indicated by arrow 710. Fluid then flows as indicated by arrow 712. As indicated by arrow 714, flow goes through a measuring loop, which may be similar to that discussed hereinbefore including a densitometer, prover, sample connections, valves, and the like. Flow then returns as indicated by arrow 716 through tube 718 which enters pipe 702 and is sealed at seal 720. Flow then continues through flowline 706 as indicated by arrow 719 and exits back into the pipeline through opening 722 as indicated by arrow 721. The sealing can be the same as discussed hereinbefore with respect to FIG. 2 utilizing a compression nut that allows orientation of scoop face 708. Bi-directional scoop 700 could also be utilized with the retractable yoke design 300 discussed hereinbefore to provide a retractable bi-directional measurement flow loop.

FIG. 8 provides a single pipe bi-directional scoop 800 that provides a mixing chamber 802 which is continuously refreshed. Prior art sampling systems that utilize a scoop suffer from the problem that stale fluid accumulates therein. Thus, fluid taken at a particular moment may not be representative of fluid in the pipeline. Since the samples are often timed, this could be problematic in verifying that the sample is valid.

Scoop 800 is comprised of single pipe 804. Scoop 800 may be sealed/oriented as discussed with respect to FIG. 2A and FIG. 2B as discussed with respect to FIG. 7 or using other seals as desired. Fluid enters scoop face 806 from the pipeline as indicated by arrow 812. The fluid travels up flow path 808 and enters mixing chamber 802 as indicated by arrow 814. The fluid in mixing chamber 802 is thereby continuously refreshed. Fluid exits mixing chamber 802 via tube 820 and flows in the direction of arrow 816 through flow path 810. Fluid exits single pipe 804 as indicated by arrow 818 through opening 822.

Accordingly, the present invention provides a highly desirable scoop design 10 as indicated in FIG. 1A and FIG. 1B, a seal and orientation apparatus as indicated in FIG. 2A and FIG. 2B, a retractable scoop design shown in FIG. 3A, FIG. 3B, FIG. 3C, FIG. 3D, compact single flange bi-directional tandem mounted scoops as indicated by FIG. 4, FIG. 5, FIG. 6, and FIG. 9A, and single pipe bi-directional scoops as indicated by FIG. 7 and FIG. 8.

The foregoing description of the preferred embodiments of the invention has been presented for purposes of illustration and description only. It is not intended to be exhaustive or to limit the invention to the precise form disclosed; and obviously many modifications and variations are possible in light of the above teaching. Such modifications and variations that may be apparent to a person skilled in the art are intended to be included within the scope of this invention as defined by the accompanying claims.

The invention claimed is:

1. A bidirectional flow scoop mountable to a pipeline operable for receiving and returning a fluid from a fluid flow in said pipeline, said pipeline being operable for transmitting said fluid that comprises at least one of oil, gas, or petroleum products, said pipeline comprising a pipeline wall defining an opening, said bidirectional flow scoop comprising:

a first tubular comprising a scoop end, a mounting for connection to said opening operable to support said first tubular when said first tubular extends into said pipeline to receive a sample of at least one of said oil, gas, or petroleum products, said scoop end comprising a bend that ends with a first opening for said fluid flow, said bend comprises a bend radius in an axis through said first tubular greater than a diameter of said first tubular, said first tubular comprising a first outlet distal said first opening, said first outlet being positioned outside of said pipeline when said bidirectional flow scoop is mounted to said pipeline;

a second tubular mounted within said first tubular with said bend defining a second opening, said second tubular comprising a second outlet distal said second opening, said second outlet being positioned outside of said pipeline when said bidirectional flow scoop is mounted to said pipeline, said first tubular and said second tubular of said bidirectional flow scoop being operable to provide fluid flow in two directions internal to said first tubular when mounted to said pipeline; and a sampling chamber, a valve connected to said sampling chamber, said first tubular is configured to receive said fluid from said pipeline which enters said sampling chamber and said second tubular is configured to return said fluid to said pipeline without going through said valve so that when said valve is closed then fluid in said sampling chamber is continuously refreshed to be representative of said fluid in said pipeline, when said valve is open then said fluid in said sampling chamber flows through said valve.

2. The bidirectional flow scoop of claim 1, wherein said second tubular comprises a second rounded bend within an axis of said second tubular.

3. The bidirectional flow scoop of claim 1, wherein said first tubular comprises a wall opening in a wall of said first tubular at a position external to said pipeline when said first tubular is mounted to said pipeline, said second tubular extends through said wall opening of said first tubular, and a metallic seal where said second tubular extends through said wall opening in said wall of said first tubular.

4. The bidirectional flow scoop of claim 1 further comprising said first opening is elliptical.

5. The bidirectional flow scoop of claim 1, further comprising a compression nut mounted to said first tubular wherein said compression nut compresses a ferrule which seals between a fitting and an outer surface of said first tubular, said compression nut being rotatable to compress said ferrule that engages a wall of said first tubular and when compressed produces an initial seal which allows rotation of said first tubular to orient said first tubular in said pipeline.

6. The bidirectional flow scoop of claim 3, further comprising a flow loop comprising at least one of a densitometer or a prover, said first outlet and said second outlet being connected to said flow loop.

7. A method for providing a bidirectional flow scoop mountable to a pipeline operable for receiving and returning a fluid from a fluid flow in said pipeline, said pipeline being operable for transmitting said fluid that comprises at least one of oil, gas, or petroleum products, comprising the following steps:

utilizing a pipeline wall for a pipeline connection of said bidirectional flow scoop to said pipeline wherein said pipeline wall comprises a wall portion that is continuous without an inserted T-section from upstream of a threaded pipeline connection for said bidirectional flow scoop to downstream of said threaded pipeline connection;

providing a first tubular that comprises a scoop end which is operable to be mounted to said pipeline connection so that said first tubular extends into said pipeline to receive a sample of at least one of said oil, gas, or petroleum products, from said pipeline;

providing that said first tubular comprises a bend that leads to a face, said face defining a first opening for said fluid flow;

providing that said first tubular comprises a first outlet distal said first opening, said first outlet being positioned outside of said pipeline when said bidirectional flow scoop is mounted to said pipeline;

providing a second tubular mounted within said first tubular with a second opening that extends through said bend;

providing that said second tubular comprises a second outlet distal said second opening;

providing that said second tubular has a length so that said second outlet is positioned outside of said pipeline when said bidirectional flow scoop is mounted to said pipeline;

providing that said first tubular and said second tubular of said bidirectional flow scoop are operable to provide fluid flow in two directions internal to said first tubular when mounted to said pipeline;

metallically sealing said first tubular at said second outlet that is formed through an opening in a wall of said first tubular, said second tubular extending through said opening in said wall of said first tubular; and providing a sample chamber connected to said first tubular and said second tubular to continually refresh said fluid in said sample chamber from said pipeline and providing a valve connected to said sample chamber operable for releasing a sample of said fluid when said valve is open, said valve being connected externally of fluid flow to and from said sample chamber so that when said valve is closed then said first tubular and said second tubular continue to refresh said fluid in said sample chamber.

8. The method of claim 7, further comprising providing a flow loop comprising at least one of a densitometer or a prover, said first outlet and said second outlet being connected to said flow loop.

9. The method of claim 7, further providing a compression nut mounted to tighten a metallic ferrule to producer an initial seal that allows said bidirectional flow scoop to be oriented within said pipeline.

10. The method of claim 7, further comprising providing a second rounded bend within an axis of said second tubular.

* * * * *